United States Patent
Pokropinski et al.

[11] Patent Number: 6,083,243
[45] Date of Patent: Jul. 4, 2000

[54] ETHYLENE-PROPYLENE COATINGS FOR SUTURES

[75] Inventors: Henry Pokropinski, South River; Alastair W. Hunter, Bridgewater; Karl W. Brennan, Somerset; Dennis D. Jamiolkowski, Long Valley, all of N.J.

[73] Assignee: Ethicon, Inc., Somerville, N.J.

[21] Appl. No.: 09/145,319

[22] Filed: Sep. 1, 1998

[51] Int. Cl.[7] .................................................. A61B 17/04
[52] U.S. Cl. ........................................... 606/230; 606/228
[58] Field of Search ..................................... 606/228, 229, 606/230, 231

[56] References Cited

U.S. PATENT DOCUMENTS 4,543,286  9/1985  Harpell et al. .......................... 428/288
4,563,392  1/1986  Harpell et al. .......................... 428/394
5,718,251  2/1998  Gray et al. .............................. 132/321

*Primary Examiner*—Michael Buiz
*Assistant Examiner*—Kevin Truong

[57] ABSTRACT

A suture having a coating thereon of an ethylene-propylene copolymer, and a method of coating a suture which comprises the steps of coating the surface of the suture with an effective amount of a solution of ethylene-propylene copolymer in an organic solvent, and then removing the solvent from the coated suture. The copolymer preferably has an average molecular weight of from about 25,000 to about 500,000 g/mole, and a mole percentage of about 55 to 70 percent ethylene and about 30 to 45 percent propylene. The coating provides an alternative to silicone, which has previously been used as a coating for sutures, and exhibits excellent performance properties, such as tactile smoothness, pliability, and knot tiedown performance.

12 Claims, No Drawings

ETHYLENE-PROPYLENE COATINGS FOR SUTURES

FIELD OF THE INVENTION

The present invention relates to coated surgical sutures. More specifically, it relates to sutures coated with an ethylene-propylene copolymer coating.

BACKGROUND OF THE INVENTION

Surgical sutures often require a surface coating to improve one or more of their performance properties. For example, a multifilament suture typically requires a surface coating to improve the tactile smoothness, and tiedown performance of the suture, so it passes easily and smoothly through tissue during operative procedures In response to the need for suitable coatings for surgical sutures, numerous patents have disclosed potential coating compositions. U.S. Pat. No. 3,942,532 discloses a polyester coating for multifilament sutures. The preferred polyester coating is polybutilate, which is the condensation product of 1,4-butanediol and adipic acid. U.S. Pat. No. 4,105,034 discloses a multifilament suture coating of a poly(alkylene oxalate), e.g., poly(hexamethylene oxalate). Although the coating compositions disclosed in these patents exhibit excellent handling characteristics and enhance many of the properties of the coated suture, the knot integrity of the coated suture diminishes slightly.

U.S. Pat. No. 3,527,650 discloses a coating composition of polytetrafluoroethylene (PTFE) particles in an acrylic latex. Although PTFE acts as an excellent lubricant to decrease the roughness of multifilament sutures, it has a tendency to flake off during use. Also, this particular coating is a thermoset which requires a curing step for proper application. U.S. Pat. No. 4,043,344 discloses a PLURONICS ethylene oxide/propylene oxide copolymer for nonabsorbable surgical sutures. Unfortunately, these copolymer coatings lose their lubricity during wet tiedown evaluations—most likely due to their tendency to also come off during use.

Silicone has previously been used as a coating for sutures. It is desirable, however, to develop a non-silicone based suture coating which had the same lubrication properties as silicone. Efforts at using existing coatings on sutures previously coated with silicone, or developing a new, non-silicone replacement coating which meets the coating performance properties of silicone, have until now been unsuccessful. Many of these coatings were derived from wax-like based materials.

In view of the deficiencies with the potential candidates for suture coatings, and in view of the desire for non-silicone based coatings, it would be desirable to develop a coating for a suture that can be applied using conventional techniques, and that exhibits all of the superior performance properties which silicone coatings possess (improved tactile smoothness of the coated suture, pliability and knot integrity).

It is therefore an object of the present invention to provide a coated suture which exhibits excellent performance properties, such as tactile smoothness, pliability, and knot tiedown performance.

It is a further object of the present invention to provide a suture having its surface coated with a non-silicone based coating for lubricating the suture surface.

These and other objects and advantages of the invention will become more fully apparent from the description and claims which follow or may be learned by the practice of the invention.

SUMMARY OF THE INVENTION

The present invention is directed to a coated suture. The suture is coated on its surface with an amount of ethylene-propylene copolymer effective to replace silicone as a suture coating. The copolymer has an average molecular weight of from about 25,000 to about 500,000, and a mole percentage of about 55 to 70 percent ethylene, preferably 45–60 wt. % ethylene and most preferably 50–55 wt. percent ethylene and about 45 to 30 percent propylene, preferably 40 to 55 wt. percent propylene and most preferably 45–50 wt. percent propylene. The coated suture exhibits excellent performance properties, such as tactile smoothness, pliability, and knot tiedown performance.

In another aspect, the invention is a method of coating a suture which comprises the steps of coating the surface of the suture with an effective amount of a solution of ethylene-propylene copolymer in an organic solvent, and then removing the solvent from the coated suture. The copolymer preferably has an average molecular weight of from about 100,000 to about 300,000, and a mole percentage of about 60 to 65 percent ethylene and about 35 to 40 percent propylene.

DETAILED DESCRIPTION OF THE INVENTION

Ethylene-propylene (EPM) copolymers within the scope of this invention are known and can be prepared by conventional techniques. The EPM copolymer is represented by repeating units of the formula:

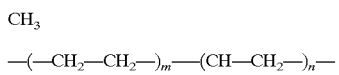

EPM copolymers are elastomers, i.e., they are polymeric materials that rapidly recover their shape after removal of a strain of at least 50%, and their entropically derived equilibrium modulus increases with temperature. There are various grades of EPM copolymers, which offer systematic variations in molecular characteristics, which in turn lead to differences in processing, cure characteristics, and performance. Ethylene-propylene elastomers are not toxic and are flammable only after heating to thermal-decomposition temperatures, e.g., >300° C. Certain grades have received FDA approval for contact with the skin and in pharmaceutical applications. Olefin comonomers may be added to further modify the EPM chain.

The EPM copolymers of this invention generally have a mol percentage of from about 55 to about 70 percent ethylene and from about 30 to about 45 percent propylene, preferably about 60 to about 65 mole percent ethylene and about 35 to about 40 mole percent propylene, and most preferably 60 percent ethylene and 40 percent propylene.

The EPM copolymers of this invention are typically characterized by a weight average molecular weight as determined by gel permeation chromatography ranging from about 25,000 to about 500,000, preferably from about 100,000 to about 300,00, and most preferably about 120,000 to about 250,000 g/mole. An EPM copolymer with too low a molecular weight may fail to significantly improve the knot tiedown of a coated suture, and an EPM copolymer with molecular weight too high may increase the stiffness of the coated suture.

The amount of EPM copolymer coated onto the surface of the suture to provide a non-silicone replacement coating with equivalent or superior performance properties will generally depend on the molecular weight of the EPM copolymer and can readily be determined empirically. In most instances, the required amount of EPM copolymer decreases as its molecular weight increases. Advantageously, the amount of EPM copolymer coated onto the suture ranges from about 0.5 to about 15 percent, preferably from about 2 to about 9, and most preferably about 3 to 7 percent of the weight of the coated suture. Generally, too high a weight percent may compromise the knot security of the coated suture and too low a weight percent may fail to achieve the desired level of suture properties. The amount required to achieve optimum performance may depend on the suture size and type; smaller sizes may require a greater weight percent add on.

Sutures within the scope of this invention can be of any type used or contemplated for operative procedures. The suture can be synthetic or natural, absorbable or nonabsorbable, or a monofilament or multifilament in a braided, twisted, or covered form. Bicomponent sutures, such as those of the core-sheath type, may also be used. In addition, the sutures can be attached to one or more needles, if desired. Examples of absorbable monofilament sutures include natural sutures such as surgical gut and collagen, and synthetic sutures such as homopolymers and copolymers of p-dioxanone. Examples of absorbable multifilament sutures include sutures prepared from fiber-forming polymers of one or more lactones, e.g., VICRYL® poly(lactide-co-glycolide) multifilament sutures. Examples of nonabsorbable monofilament and multifilament sutures include nylon, polypropylene, steel, polyvinylidene fluoride, linen, cotton, silk, and polyesters such as polyethylene terephthalate (PET). The preferred sutures are nonabsorbable, multifilament sutures, preferably braided silk sutures.

The organic solvent for the EPM copolymer coating of this invention is advantageously a solvent which has a normal boiling point no greater than 120° C. Examples of suitable organic solvents include but are not limited to chlorinated aliphatic solvents such as 1,1,2-trichloroethane and aromatic solvents such as toluene, benzene, xylene and blends thereof The solvent system is selected, in part, so as to minimize disadvantageous interactions with the suture substrate.

The coating can easily be prepared by simply dissolving the EPM copolymer into the appropriate organic solvent. The concentration of the copolymer in solution will, of course, depend on the amount of copolymer desirably coated onto the surface of the suture and the size of the suture, but generally should range from about 0.25 to about 6 weight percent, preferably from about 2 to about 4 weight percent, and most preferably about 3 weight percent.

Once a solution of the EPM copolymer is prepared, a suture can be coated using conventional coating techniques, e.g., by dipping, spraying, etc. After the coating is applied, the solvent can be removed by drying in air, or by other techniques well known in the art, for example, removing the solvent at an elevated temperature under vacuum. It should be apparent to those skilled in the art, that the coatings of the subject invention can be applied by solventless techniques such as hot melt coating.

The following example illustrates but is in no way intended to limit the scope of the claimed invention. In the example, the tensile properties, tiedown roughness and knot security are each determined using an Instron Tensile Tester. The tensile properties, i.e., the straight and knot tensile strength and the percent elongation, are determined generally according to the procedures described in U.S. Pat. No. 4,838,267. The tiedown roughness is a measure of the knot tiedown performance. It provides an indication of the force required to slide a knot down a suture, and it is determined generally according to the procedure described in U.S. Pat. No. 3,942,532. The knot security, which provides an indication as to the number of throws required to secure a knot so that it fails to slip before cleanly breaking, is measured by first tying a conventional square knot around a mandrel, pulling the knot apart on the Instron Tester to observe whether slipping occurs, and if so, then tying knots with additional throws until 20 out of 20 knots break cleanly without slipping.

EXAMPLE

The EPM is a copolymer with a 170,000 weight average molecular weight and has a mole percent of 60 percent ethylene and 40 percent propylene. The EPM copolymer was obtained from Scientific Polymer Products, Inc. of Ontario, N.Y. and came in pelletized form. The EPM copolymer is soluble in toluene solvent and is prepared at a 3.0 percent w/w concentration in toluene for the experimental coating runs. A size 7/0 uncoated black braided silk suture is double coated at the 3.0 percent w/w level of coating. This method was selected to achieve the desired solids add-on to give tiedown properties similar to silicone-coated 7/0 silk sutures. The suture is coated at room temperature with the coating solution using conventional laboratory coating equipment, and the coated suture is subsequently dried in air at 110° F. to remove the toluene. Table I compares the tensile and tiedown roughness properties and the knot security characteristics for the EPM coated suture with a size 7/0 uncoated black braided silk suture, a size 7/0 wax coated black braided silk suture, and a size 7/0 silicone coated black braided silk suture. Each of the sutures, except for the uncoated suture, were cobalt sterilized.

TABLE I

Physical Properties of Cobalt 60 Sterilized 7/0 Black Braided Silk Sutures, Coated With Wax, EPM Resin, and Silicone Resin, and Compared to Uncoated 7/0 Black Braided Silk Suture Non-Irradiated Control

| PROPERTY | 7/0 Uncoated Black Braided Silk | 7/0 Wax Coated Black Braided Silk | 7/0 EPM Coated Black Braided Silk | 7/0 Silicone Coated Black Braided Silk |
| --- | --- | --- | --- | --- |
| Percent Coating Solids (wt/wt) | — | 10.1% | 5.8% | 6–8% (est.) |
| Subjective Wet and Dry Tiedown Properties | — | Smoother in wet and dry tiedown vs. control | Appreciably smoother in wet and dry tiedown vs. control | slightly smoother in wet and dry tiedown vs. control |

TABLE I-continued

Physical Properties of Cobalt 60 Sterilized 7/0 Black Braided Silk Sutures, Coated With Wax, EPM Resin, and Silicone Resin, and Compared to Uncoated 7/0 Black Braided Silk Suture Non-Irradiated Control

| PROPERTY | 7/0 Uncoated Black Braided Silk | 7/0 Wax Coated Black Braided Silk | 7/0 EPM Coated Black Braided Silk | 7/0 Silicone Coated Black Braided Silk |
|---|---|---|---|---|
| Suture Diameter (mils) | 2.46 | 2.59 | 2.44 | 2.53 |
| Knot Strength (lbs.) | 0.44 | 0.35 | 0.44 | 0.42 |
| Knot Strength Intrinsic (psi) | 93,210 | 65,920 | 94,150 | 83,580 |
| Straight Strength (lbs.) | 0.56 | 0.53 | 0.54 | 0.57 |
| Straight Strength Intrinsic (psi) | 118,870 | 100,150 | 115,410 | 113,990 |
| Elongation-to-Break (%) | 7.03 | 9.75 | 7.16 | 8.34 |

The results indicate that the black braided silk suture coated with EPM copolymer exhibits significantly improved properties relative to that of the uncoated suture, including subjective wet and dry tiedown. Furthermore, the EPM coated suture exhibits across-the-board performance properties which are nearly equal to or better than those exhibited by the silicone coated suture. Intrinsic (corrected for cross-sectional area) strength, especially knot, were particularly good.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. A coated suture comprising:
   (a) a suture; and
   (b) a coating on said suture, said coating comprising an ethylene-propylene copolymer having a weight average molecular weight of from about 25,000 to about 500,000 g/mole.

2. The coated suture of claim 1, wherein said copolymer has a weight average molecular weight of from about 100,000 to about 300,000 g/mole.

3. The coated suture of claim 2, wherein said copolymer has a weight average molecular weight of about 120,000 to about 250,000 g/mole.

4. The coated suture of claim 1, wherein the copolymer has a mole percentage of from about 55 to about 70 percent ethylene and from about 30 to about 45 percent propylene.

5. The coated suture of claim 4, wherein the copolymer has a mole percentage of from about 60 to about 65 percent ethylene and from about 35 to about 40 percent propylene.

6. The coated suture of claim 5, wherein the copolymer has a mole percentage of about 60 percent ethylene and about 40 percent propylene.

7. The coated suture of claim 1, wherein said copolymer is present on said suture in an amount of from about 0.5 to about 15 percent of the weight of said coated suture.

8. The coated suture of claim 7, wherein said copolymer is present on said suture in an amount of from about 2 to about 9 percent of the weight of said coated suture.

9. The coated suture of claim 8, wherein said copolymer is present on said suture in an amount of about 3 to about 7 percent of the weight of said coated suture.

10. The coated suture of claim 1, wherein said suture is a nonabsorbable suture.

11. The coated suture of claim 10, wherein said suture is a silk suture.

12. The coated suture of claim 11, wherein said suture is a braided suture.

* * * * *